United States Patent [19]

Mock et al.

[11] Patent Number: 5,155,216
[45] Date of Patent: Oct. 13, 1992

[54] NUCLEIC ACIDS LABELED WITH A CHEMILUMINESCENT ACRIDINE ESTER

[75] Inventors: Graham A. Mock, Northboro; Michael Septak, Ashland; Michael J. Powell, Franklin, all of Mass.

[73] Assignee: Amoco Corporation, Chicago, Ill.

[21] Appl. No.: 682,873

[22] Filed: Apr. 8, 1991

Related U.S. Application Data

[63] Continuation of Ser. No. 128,330, Dec. 3, 1987, abandoned, which is a continuation-in-part of Ser. No. 766,038, Aug. 15, 1985, abandoned.

[51] Int. Cl.$^5$ .................. C07H 17/00; C07H 19/06; C12Q 1/68; C12P 19/34
[52] U.S. Cl. .................................... 536/24; 435/6; 435/89; 435/91; 536/23; 536/26; 935/78
[58] Field of Search ............ 435/6, 89, 91; 436/27, 436/800; 536/23, 24, 26; 935/77, 78

[56] References Cited

U.S. PATENT DOCUMENTS

| | | | |
|---|---|---|---|
| 3,539,574 | 11/1970 | Sheehan et al. | 260/279 |
| 4,259,313 | 3/1981 | Frank et al. | 424/8 |
| 4,283,382 | 8/1981 | Frank et al. | 424/8 |
| 4,352,751 | 10/1982 | Wieder et al. | 260/112 R |
| 4,374,120 | 2/1983 | Soini et al. | 436/546 |
| 4,432,907 | 2/1984 | Wieder et al. | 260/429.2 |
| 4,478,817 | 10/1984 | Campbell et al. | 424/7.1 |
| 4,547,569 | 10/1985 | Letsinger et al. | 536/29 |
| 4,563,419 | 1/1986 | Ranki et al. | 435/6 |
| 4,707,352 | 11/1987 | Stavrianpoulos | 435/26 X |
| 4,707,440 | 11/1987 | Stavrianopoulos | 435/6 |

FOREIGN PATENT DOCUMENTS

| | | |
|---|---|---|
| 0064484 | 11/1982 | European Pat. Off. |
| 0068875 | 1/1983 | European Pat. Off. |
| 0082636 | 6/1983 | European Pat. Off. |
| 0103558 | 3/1984 | European Pat. Off. |
| 8403285 | 8/1984 | PCT Int'l Appl. |
| 1461877 | 1/1977 | United Kingdom |

OTHER PUBLICATIONS

Langer et al. (1981) PNAS 78, 6633.
Weeks et al. (1983) Clin. Chem. 29, 1474.
Gaglias et al. (1979) Monatshefte fur Chemie 110, 763.
Gross, et al, Biochimica et Biophysica Acta vol. 656, 1981, pp. 167–176.

*Primary Examiner*—David M. Naff
*Attorney, Agent, or Firm*—Norval B. Galloway; William H. Magidson; Frank J. Sroka

[57] ABSTRACT

Polynucleotides are labeled with chemiluminescent acridine esters or luminescent lanthanides. Labelling is preferably carried out by incorporating a functional group into a nucleotide or polynucleotide at the C4 position of the pyrimidine portion or the C6 position of the purine portion and bonding a chemiluminescent acridine ester or a luminescent lanthanide to the functional group. The labeled polynucleotides are useful for direct detection of homologous polynucleotide sequences.

11 Claims, No Drawings

NUCLEIC ACIDS LABELED WITH A CHEMILUMINESCENT ACRIDINE ESTER

This is a continuation of copending application Ser. No. 07/128,330 filed on Dec. 3, 1987, now abandoned, which is a continuation-in-part of Mock et al., application Ser. No. 06/766,038, entitled LABELED NUCLEIC ACIDS, filed Aug. 15, 1985, now abandoned, and hereby incorporated by reference.

BACKGROUND OF THE INVENTION

This invention relates to the nonisotopic labeling of nucleic acids.

The labeling of nucleic acids is essential for many analytical purposes in both medicine and research. For example, such labeled molecules can be used to detect the presence of a single copy of a gene of a specific organism, within a complex group of organisms, and thus allow rapid diagnosis of infections. Traditionally such labeling has involved the enzymic incorporation of radioactively labeled nucleotides into nucleic acids, using DNA polymerase.

Nonisotopic methods of labeling nucleic acids also exist. One such method entails the incorporation of biotin-labeled nucleotides into nucleic acid (Langer et al. 1981 Proceedings of National Academy of Sciences, 78, 6633). After hybridization of this labeled nucleic acid to target DNA bound to a filter, it can be detected by a colorimetric assay (e.g., Landes U.S. Pat. No. 4,626,501). This assay involves the formation of a complex of the biotin with avidin; the addition of a biotin-labeled enzyme such that the enzyme complexes to the avidin; and the detection of the enzyme by the addition of a colorimetric substrate.

SUMMARY OF THE INVENTION

This invention provides polynucleotides labeled with acridine esters or, luminescent lanthanides. These labeled polynucleotides provide a tool for the direct detection of homologous polynucleotide sequences.

The method of synthesizing nonisotopically labeled polynucleotides by incorporating esters of acridinium-9-carboxylic acid (acridine esters); (Campbell et al., European Patent No. 0082636), or luminescent lanthanides (Hemmila, European Patent No. 064484), most preferably europium, terbium or samarium, into the polynucleotide, generally involves the incorporation of functionalizing reagents into the polynucleotide and the subsequent linkage of an acridine ester, a luminescent lanthanide, or a luminescent lanthanide chelate to these reagents. These functionalizing reagents may be incorporated either chemically or enzymically. In one embodiment analogs of cytosine are chemically added during the synthesis of a polynucleotide and in another DNA polymerase is used to incorporate analogs of, e.g., triphosphorylated bases into a polynucleotide that is synthesized from a single or double stranded template. Examples of such triphosphorylated bases are shown below:

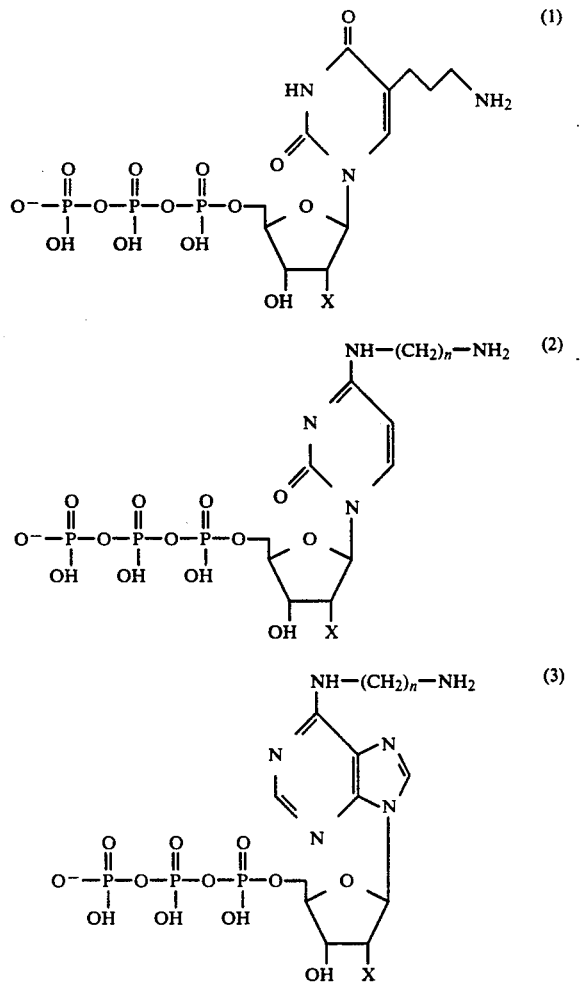

where X is H or OH and $2 \leq n \leq 10$. Another method involves the covalent attachment of a previously labeled nucleotide or polynucleotide to an existing polynucleotide by, e.g., carbodiimide coupling.

The labeled polynucleotides can be used in standard procedures for the direct detection of homologous sequences of RNA or DNA on suitable media, such as nitrocellulose, without the need for the addition of enzymes or enzyme substrates.

Other features and advantages of the invention will be apparent from the following description of the preferred embodiments thereof, and from the claims.

DESCRIPTION OF THE PREFERRED EMBODIMENTS

The term "polynucleotides" refers to nucleotide sequences containing two or more nucleotide base pairs. These may be synthesized chemically without a template, or enzymically using a single or double stranded polynucleotide template, or may be derived from native sequences existing as genes, or parts of genes, in a genome, plasmid, virus, or other vector. According to the invention, polynucleotides are labeled with one or more acridine ester groups, or luminescent lanthanides.

ACRIDINE ESTERS

Acridine esters and their synthesis have been described in Campbell et al., id., McCapra et al. British Patent No. 1,461,877, and Sheehan U.S. Pat. No. 1,461,877, and Sheehan U.S. Pat. No. 3,539,574, both hereby incorporated by reference. Acridine esters useful in the invention are chemiluminescent and have the general formula:

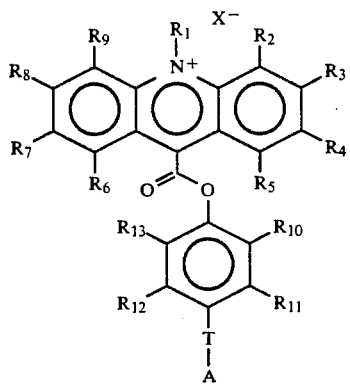
(4)

where a) each $R_1$-$R_{13}$, may be the same or different and may be H, alkyl (aliphatic carbon chain, straight or branched, of 1 to 20 carbon atoms), alkenyl (same as alkyl, except containing one or more carbon-carbon double bonds), alkynyl (same as alkyl, except containing one or more carbon-carbon triple bonds), aryl (containing an aromatic group, e.g., phenyl, napthyl, etc., which may itself be substituted with any of the other functional groups listed herein as possible R groups), hydroxyl, oxy anion, alkyloxy, aryloxy, amino, aklylamino, arylamino, dialkylamino (where the alkyl groups may be the same or different), diarylamino (where the aryl groups may be the same or different), halide (e.g., F, Cl, Br or I), thiol, alkylthiol, carboxamide, carboxylate, carboxylic alkyl ester, sulfonamide, sulfonate, sulfonate alkyl ester, sulfoxide, or sulfone, provided that such R groups must not collectively increase molecular weight to the point where the acridine ester molecule is insoluble. Most preferred R groups are H, $CH_3$, $CH_2CH_3$ thiol, Cl, and phenyl.

b) T may be any divalent (-diyl-) linker group. T may adopt any divalent form of any of the substituent groups listed above as possible R groups. For example, just as an R group may be methyl or ethyl, T may be methylene (—$CH_2$—) or ethylene (—$CH_2$—$CH_2$—). Other divalent T examples are: oxyl (—O—), alkyl oxyl [—$(C_2)_q$—O—, where q is an integer from 1 to 20], and alkyloxy alkyl [—$(CH_2)_r$—O—$(CH_2)_t$—, where r and t are integers from 1 to 20, and can be the same or different]. The length of T must be such that it does not hinder the hybridization of homologous polynucleotides significantly. Preferably, the number of carbon atoms in the aliphatic chain of T is between 1-10, and most preferably between 2 and 5.

c) A may be —(C=O)—E where E is a leaving group; most preferably, E is:

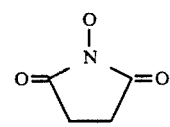
(5)

A may also be isocyanate, thiocyanate, cyanate, isothiocyanate, sulfonyl halide (e.g., —$SO_2$—Cl), or alternatively A may be an imidate ester of the form:

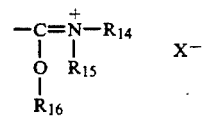

where $R_{14}$, $R_{15}$, and $R_{16}$ are defined as for the above $R_{1-13}$ groups, and again they may be the same or different.

d) X is nothing, or a counterion such as halide, perchlorate, tetrafluoroborate, sulfate, fluorosulfonate, methosulfate, methosulfonate, nitrate, acetate, alkylcarboxylate, arylcarboxylate or phosphate.

e) E may be N-hydroxysuccinimidyl, imidazolyl, triazolyl, nitrotriazolyl, tetrazolyl, N-hydroxyphthalimidyl or halomethyl (e.g., —$CH_2$—Br).

One particularly preferred acridine ester has the following substituents:
$R_1$ = methyl
each $R_2$-$R_{13}$ = H
T = ethylene (diyl, i.e., —$CH_2$—$CH_2$—)
A = —(C=O) —E, where E = N-hydroxysuccinimidyl

LUMINESCENT LANTHANIDE

The luminescent lanthanides generally are used as chelates. Examples of lanthanide chelates are given in Hemmila, id., Hindshure et al., European Patent No. 0068875, Soini et al. U.S. Pat. No. 4,374,120; Frank et al. U.S. Pat. No. 4,283,382; Frank et al. U.S. Pat. No. 4,259,313; Wieder et al. U.S. Pat. No. 4,352,751; Wider et al. U.S. Pat. No. 4,432,907; and Soini et al. European Patent No. 0103558; the above are hereby incorporated by reference. The chelating agents used in the invention must have the following properties: (a) one end of the molecule must be able to chelate a luminescent lanthanide, and (b) the other end of the molecule must have a group which is able to combine covalently with an amine, aminopropyl, or other reactive group on a polynucleotide sequence. Generally, these chelating agents have one of the two following structures;

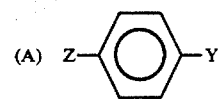
(6)

where Z is (a)

$N = C = S$, (b)

-continued

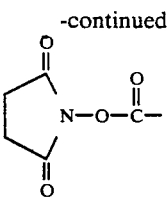

(c)

$N_3$, (d)

—$(CH_2)_n$—C—OV
  ‖
  NH where V is an alkyl or phenyl group,
and $1 \leq n \leq 10$, (e)

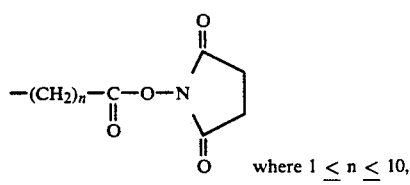

where $1 \leq n \leq 10$, (f)

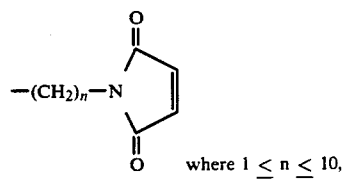

where $1 \leq n \leq 10$,

-continued (7) or (g) —$CH_2$—C—$CH_2$—W    where W is a halogen, (11)
             ‖                  preferably bromine;
             O and where Y is a polyamino carboxylate ligand, preferably

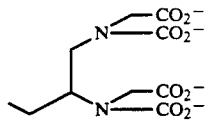  (12)

or

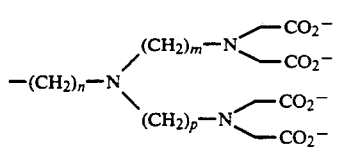  (13)

where each of n, m and p, independently, is between 2—4 inclusive; or (B) DTPAA, of the structure

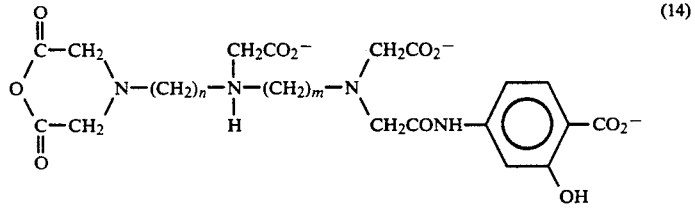  (14)

where $2 \leq n \leq 10$ and $2 \leq m \leq 4$. The chelating agents shown in (A) can be synthesized from commercially available compounds, as is generally described in Hemmila et al., (1984, Analytical Biochemistry 137:335). The synthesis of DTPAA (shown in B above) is given in M. P. Bailey et al., 1984, Analyst, 109, 1449. When the polynucleotide is to be labeled with a chelate where Z is as shown in formula (10) above, then the polynucleotide must firstly be reacted with imino thiolane before the chelate can be attached.

(8) Synthesis

Introduction of Functional Groups

The polynucleotide to be labeled must firstly be functionalized by the introduction of one or more reactive groups, such as aminopropyl or primary amine groups
(9) capable of reacting with acridine esters, or moieties able to chelate luminescent lanthanides. Such functional groups can be attached to nucleotides which are then used in the chemical or enzymic sythesis of polynucleotides. Alternatively, the functional groups can be chemically attached to existing polynucleotides.

Chemical Polynucleotide Synthesis

Base analogs such as those described by Mock (U.S. application Ser. No. 06/734,323 filed May 5, 1985, now
(10) abandoned, and assigned to the same assignee as the present application, hereby incorporated by reference) can be incorporated during synthesis of a polynucleotide, in place of the normal base. They are incorporated at the ends of the molecules, to which subsequent bases may be added as required, and function to introduce either an aminopropyl group, to which an acridine ester or luminescent lanthanide chelating compound can be attached, or a group which can be used to directly chelate a luminescent lanthanide. The general structure of such analogs is shown below:

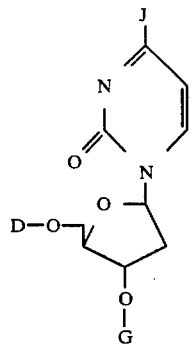 (15)

Where D is any blocking group, preferably 4, 4'-dimethoxytrityl, G is a group which enables chemical binding to other nucleotides, for example:

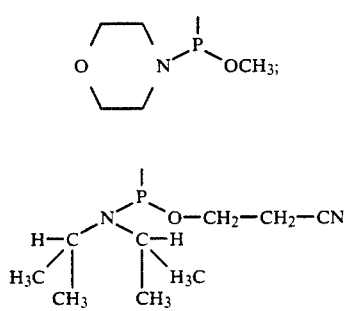 (16)

(16a)

and J is a group which can react with an acridine ester or lanthanide chelating compound, or which can chelate a luminescent lanthanide. Examples of J include:

(a) —HN(CH$_2$)n NHCOCF$_3$, where $1 \leq n \leq 10$, (a)

—NH(CH$_2$)$_n$ NHCOCF$_3$, where $1 \leq n \leq 10$, (b)

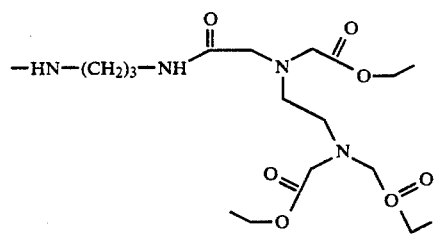 (17)

and (c)

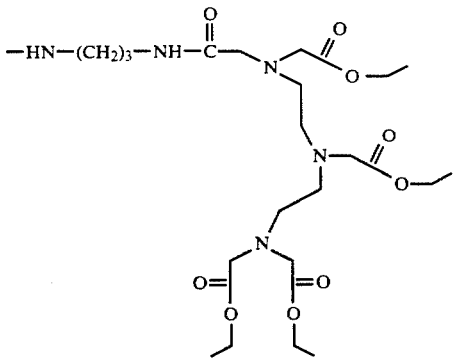 (18)

To functionalize a polynucleotide, the latter two examples (b and c) must be hydrolyzed by a base after incorporation into a synthetic polynucleotide. Such reactions result in the formation of a polynucleotide of the structure:

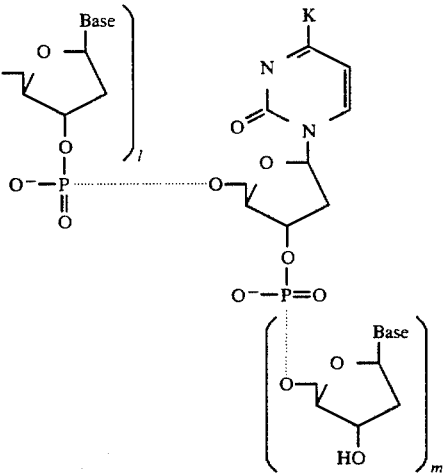 (19)

where 1 and m are 0 or a positive integer and where K is

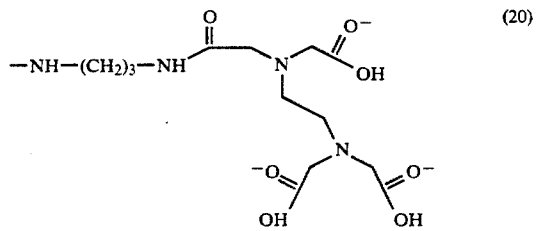 (20)

or

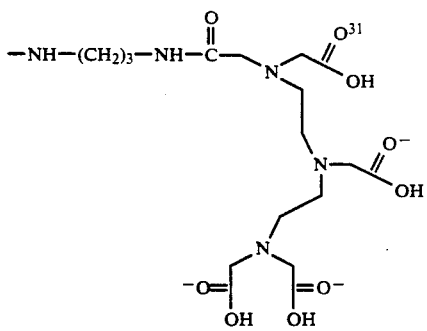

Luminescent lanthanides can be directly chelated to these latter compounds.

An example of such a chemically sythesised functionalized polynucleotide is one in which a C-4 aminopropyl-modified cytidine is incorporated at both ends of a synthetic 33 base pair polynucleotide, by automated phosphite synthesis. Such a polynucleotide has the structure:

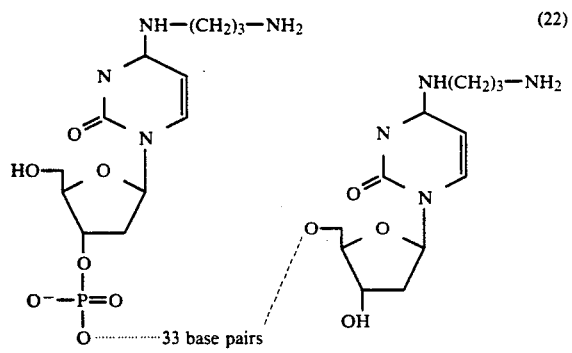

Enzymic Polynucleotide Synthesis

Modified nucleotide analogs, possessing a reactive or amino functionality, such as those shown below, can be incorporated in place of a normal triphosphorylated nucleotide base during polynucleotide labeling utilizing a single or double stranded template. Examples of such triphosphorylated nucleotides are:

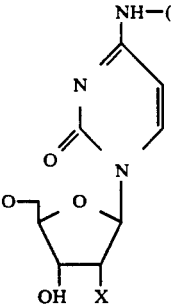

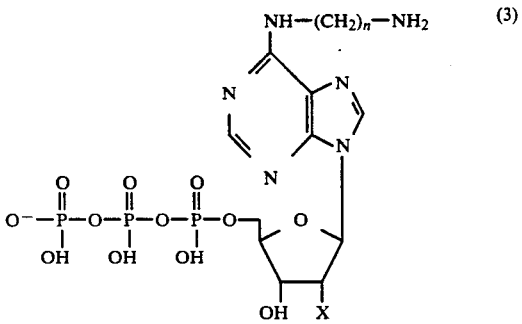

where X is H (for DNA) or OH (for RNA), and $2 \leq n \leq 10$.

Examples of such enzymic procedures include nick translation of double-stranded DNA using DNA polymerase, with or without DNAase I; primer extension of single-stranded DNA from a double stranded region using DNA polymerase I (Klenow fragment); terminal deoxytransferase tailing of DNA; or use of RNA polymerase, with analogs with 2' and 3' hydroxyl groups on the sugar moiety, and a single stranded DNA template, with a double stranded region (Maniatis et al. (1982) Molecular Cloning, A Laboratory Manual, Cold Spring Harbor Laboratory, Box 100, Cold Spring Harbor, N.Y.).

Functionalization of existing polynucleotides

Polynucleotides can be chemically modified by alkylation mainly at adenine and cytosine residues, for example, with BSPSE (Landes, id.). Alternatively, a previously labeled polynucleotide or polylysine can be covalently attached to a second polynucleotide using, e.g., carbodiimide coupling (Halloran et al., 1966, Journal of Immunology, 96:373). The polylysine can also be attached to the 5' end of a polynucleotide prior to labelling as described by Ward, European Patent No. 0063879, hereby incorporated by reference.

Addition of Acridine Esters

A polynucleotide functionalized with one or more reactive primary amine groups is readily labeled with an acridine ester as shown in the following example:

Before labeling of the polynucleotide the acridine ester (23) is synthesised as shown below:

Acridine 9 carboxylic acid (870 mg) is added to thionyl chloride (10 ml) and the mixture refluxed in an oil bath for three hours. The reaction mixture is evaporated in vacuo on a rotary evaporator and the dry residue redissolved in anhydrous pyridine (50 ml), with heating, below 60° C. This solution is cooled to approximately 20° C. in a water bath. p-hydroxy phenylpropionic acid n-hydroxy succinimide ester (1 g) is dissolved in anhydrous pyridine (10 ml) and added to the acridine 9 carboxylic chloride pyridine solution above, with stirring. The reaction mixture is stirred at 15°-30° C. for approximately 30 minutes and then poured into ice water (250 ml), whilst stirring. This mixture is transferred into a separating funnel and extracted with ethyl acetate (250 ml). The organic phase is separated, dried over anhydrous sodium sulphate, filtered and evaporated in vacuo. The residue is evaporated from anhydrous toluene (50 ml) three times and redissolved in anhydrous dimethoxy ethane (50 ml). The resulting solution is placed at 15°-30° C. for approximately 15 hours in a light-proof container. Any precipitate formed during this incubation is filtered away and the solution applied to a silica gel column (300 grams) and purified by flash chromography (W. C. Still et al., General of Organic Chemistry (1978), Vol. 43, 2923) with a solution of ethyl acetate and hexane (2:1) as an eluating solvent. Pure fractions are combined and filtered through a Teflon 47 mm 0.45 filter and evaporated in vacuo. The yield is approximately 36%. This is redissolved in anhydrous chloroform (25 ml) and methyl fluorosulphonate (1.1 ml) added to the mixture which is stirred at 15°-30° C. for approximately 20 hours. The precipitate formed is filtered off and washed three times with anhydrous toluene and two times with dimethoxy ethane. The dried crystals are stored desiccated and protected from the light at −20° C. The final yield is approximately 556 mg of pure acridine ester (23).

100 ug of functionalized DNA (a polynucleotide of 33 base pairs, functionalized with primary amine groups at both ends as shown in structure (22)) is mixed with water (190 ul), NaCl (10 ul of a 5M solution) and NaHCO$_3$ (25 ul of a 5% solution). Acridine ester (23) (8.3 ul of a 60 uM stock solution in dimethylformamide) is added at 0, 10, and 20 minutes.

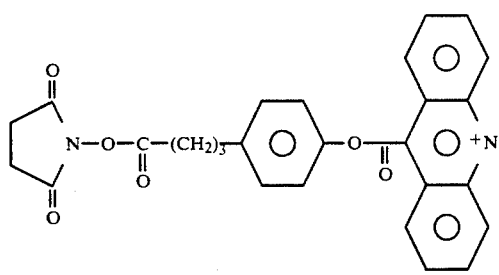
(23)

After a further 10 min, citrate (500 ul of 100 mM solution, pH 5.5), containing NaCl (200 mM), is added. The resulting labeled polynucleotide is purified over a Sephadex G25 column equilibrated with citrate (100 mM, pH 6) containing NaCl (200 mM).

This process results in a polynucleotide of the structure:

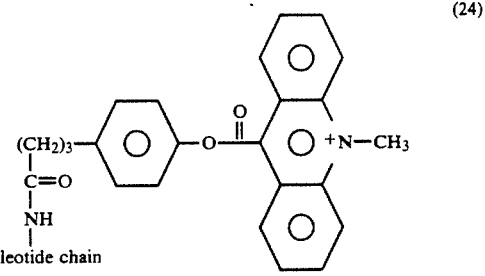
(24)

Addition of a Luminescent Lanthanide

A polynucleotide functionalized with one or more aminopropyl groups (see Mock et al. id.) is mixed with a luminescent lanthanide chelate so that the luminescent lanthanide can bind to the polynucleotide. For example, a polynucleotide 50 ug (shown in structure (22)) is mixed with triethylamine (5 ug) and the europium chelate (315 ug, dissolved in sodium borate buffer 0.2 M, pH 9.5) of formula:

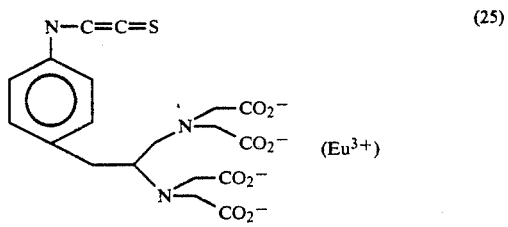
(25)

and allowed to stand for 3 hours at 15°-30° C. The labeled polynucleotide is purified over a Sephadex G50-80 column equilibrated with sodium borate (0.1 M, pH 8.0) and, if required, further purified by reverse phase hplc using a mixture of triethyl ammonium acetate (0.1 M, pH 7.0) and acetonitrile as the mobile phase. This process results in the formation of a polynucleotide of the structure:

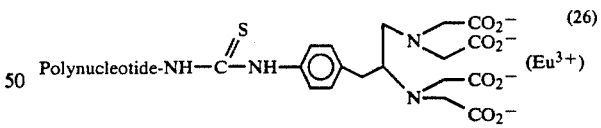
(26)

Using another starting chelate, the above process will result in the formation of polynucleotides of the structures:

Q—NH—NH—L

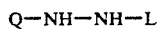

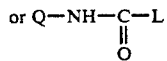

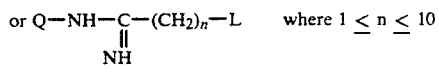  where $1 \leq n \leq 10$

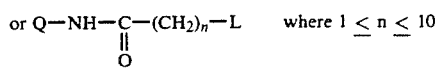  where $1 \leq n \leq 10$

-continued

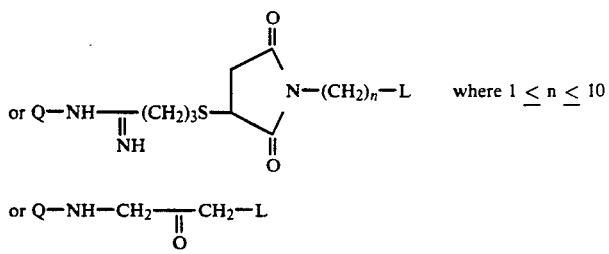

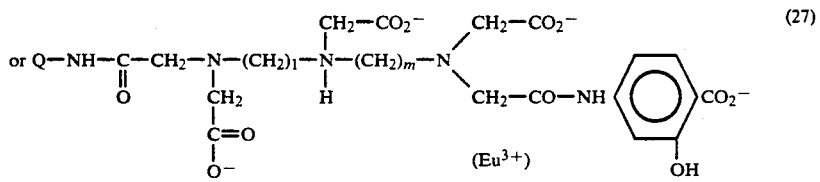

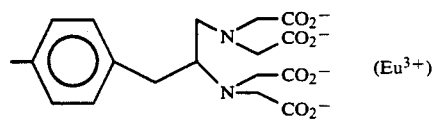

where Q is a polynucleotide,

L is

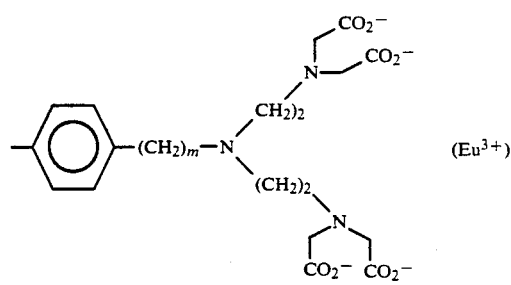

where $1 \leq n \leq 10$, $2 \leq m \leq 4$, and $2 \leq 1 \leq 10$.

Detection

(a) Luminescent Lanthanides

Hybridization of labeled polynucleotide probes to the target polynucleotide is performed by standard methodology on Pall nylon filters or their equivalent (Maniatis et al., id.). Time resolved fluorescence using an LKB fluorimeter is used to measure any bound luminescent lanthanide labeled polynucleotides, which is a measure of target polynucleotide in the sample. Enhancement of signals can be achieved by adding LKB "enhance" solution to the labeled filters.

(b) Acridine ester

Polynucleotide of samples to be tested are normally bound by standard techniques to nitrocellulose filters and then hybridized as follows:

The filters are prehybridized for 2 hours at 48° C. using 100 ul of prehybridization buffer per cubic centimeter of filter and then hybridized in buffer containing an acridine ester-labeled oligomer probe (50 ng per ml) at 48° C. for 2 hours either with or without methoxyphenazinemethylsulfate as a blocker. The prehybridization and hybridization buffers consist of tetramethyl ammonium chloride (0.9M), sodium citrate (50 mM), Denharts (5 X), SDS (0.1%), sodium pyrophosphate (0.1%), and E. coli tRNA (2 ul per ml of 50 mg/ml stock solution). The filters are then washed, at 15°-30° C. in tetramethyl ammonium chloride (0.9 M) containing sodium citrate (100 mM, pH 6.5), four times for five minutes. The areas on which the polynucleotides had been bound are then cut out and treated with sodium acetate (50 ml of 10 mM, pH 4.75) contained in 12×47 mm polystyrene tubes. Samples are measured for chemi-luminescence signal (peak area integration mode) on a Berthold 9500T photon counter using NaOH (100 ml of 0.1 M) containing hydrogen peroxide (0.1%), as injection reagent. The figures obtained are compared to those obtained from filters which contained no polynucleotide. The blocker reagent eliminates nonspecific binding.

Other embodiments are within the following claims.

We claim:

1. A method of nonisotopically synthesizing a labeled nucleotide or polynucleotide comprising:
incorporating a functional group through the C4 position of the pyrimidine portion or the C6 position of the purine portion of said nucleotide or said polynucleotide, said pyrimidine having the structure

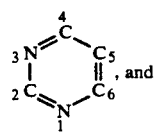, and said purine have the structure

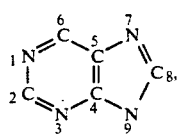

wherein the ring atoms of said pyrimidine or said purine are numbered consecutively as 1-6 and 1-9, respectively, and bonding an acridine ester to said functional group, said acridine ester being chemiluminescent.

2. The method of claim 1 wherein said acridine ester has the structure:

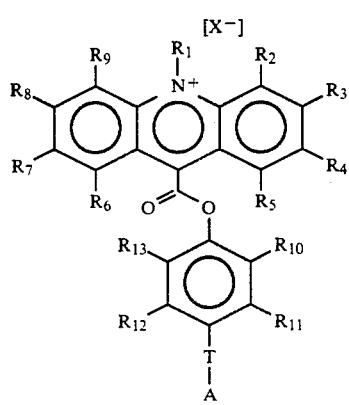

where
a) each individual $R_1$-$R_{13}$ may be the same or different, and may be H, alkyl, alkenyl, alkynyl, aryl, hydroxyl, oxy anion, alkyloxy, aryloxy, amino, aklylamino, arylamino, dialkylamino, diarylamino, halide, thiol, alkylthiol, carboxamide, carboxylate, carboxylic alkyl ester, sulfonamide, sulfonate, sulfonate alkyl ester, sulfoxide, or sulfone; provided that such R groups must not collectively increase molecular weight to the point where said acridine ester is insoluble;
b) T is any divalent linker group linking said acridine moiety to said A moiety of said formula (4), or may adopt any divalent form of any of said individual $R_{1\text{-}13}$ groups; the length of T is such that it does not hinder the hydridization of homologous polynucleotides significantly; and
c) A is —(C=O)—E, said E being N-hydroxysuccinimidyl, imidazolyl, triazolyl, nitrotriazolyl, tetrazolyl, N-hydroxyphthalimidyl or halomethyl; or isocyanate, thiocyanate, cyanate, isothiocyanate, sulfonyl halide or an imidate ester of the form:

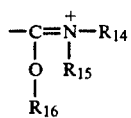

where $R_{14}$, $R_{15}$, and $R_{16}$ are as defined for $R_{1\text{-}13}$, and each individually may be the same or different.

3. The method of claim 2 wherein said E moiety is N-hydroxysuccinimide having the structure

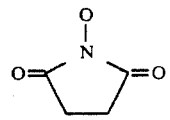

4. The method of claim 1 wherein said method comprises chemically modifying said nucleotide or said polynucleotide and linking said acridine ester to said modified nucleotide or said modified polynucleotide.

5. The method of claim 4 wherein said modifying comprises alkylation of a base of said nucleotide or polynucleotide.

6. The method of claim 2 wherein $R_1$ is methyl, T is ethylene, A is —(C=O)—E, E is N-hydroxysuccinimidyl and each $R_2$, $R_3$, and $R_4$ is H.

7. The method of claim 2, further comprising the negatively charged species $X_-$, wherein said $X^-$ is a counterion.

8. The method of claim 7, said $X^-$ being halide, perchlorate, tetrafluoroborate, sulfate, fluorosulfonate, methosulfate, methosulfonate, nitrate, acetate, alkylcarboxylate, arylcarboxylate, or phosphate.

9. A nucleotide or polynucleotide labeled with a chemiluminescent acridine ester, wherein said acridine ester is bonded to a functional group, said function group being covalently bonded to said nucleotide or said polynucleotide at the C4 position of the pyrimidine portion or the C6 position of the purine portion of said nucleotide or said polynucleotide, said pyrimidine having the structure

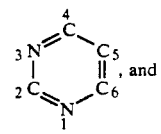

,and said purine having the structure

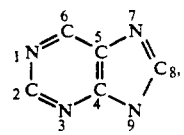

wherein the ring atoms of said pyrimidine or said purine are numbered consecutively as 1-6 and 1-9, respectively.

10. The nucleotide or polynucleotide of claim 9 wherein said acridine ester is chemically linked to a functional group, comprising an amine group, on said nucleotide or said polynucleotide.

11. The nucleotide or polynucleotide or claim 10 wherein said amine group is introduced onto said nucleotide or said polynucleotide by chemically or enzymically attaching to said nucleotide or said polynucleotide a second nucleotide or a second polynucleotide which comprises said amine group.

* * * * *